United States Patent [19]

Gessman

[11] Patent Number: 4,637,404
[45] Date of Patent: Jan. 20, 1987

[54] METHOD AND APPARATUS FOR CONVERTING A CATHETER TO A CARDIAC PACING ELECTRODE

[76] Inventor: Lawrence J. Gessman, 1929 West Point Ct., Cherry Hill, N.J. 08002

[21] Appl. No.: 543,866

[22] Filed: Oct. 20, 1983

[51] Int. Cl.$^4$ .............................................. A61N 1/05
[52] U.S. Cl. ................................ 128/786; 128/419 P
[58] Field of Search ............................. 128/784–786, 128/419 P, 642

[56] References Cited

U.S. PATENT DOCUMENTS

| 3,323,523 | 6/1977 | Scislowicz | 128/214.4 |
|---|---|---|---|
| 3,485,247 | 12/1969 | Ackerman | 128/418 |
| 3,516,412 | 6/1970 | Ackerman | 128/418 |
| 3,533,403 | 10/1970 | Woodson | 128/2.06 |
| 3,561,445 | 2/1971 | Katerndahl et al. | 128/214.4 |
| 4,072,146 | 2/1978 | Howes | 128/674 |
| 4,214,594 | 7/1980 | Little | 128/786 |
| 4,271,847 | 6/1981 | Stokes | 128/786 |
| 4,280,503 | 7/1981 | Ackerman | 128/419 |
| 4,383,532 | 5/1983 | Dickhudt | 128/419 P |

OTHER PUBLICATIONS

Letter to the editor entitled "Emergency Cardiac Pacing", by Colquhoun, M., appearing in the British Medical Journal No. 287(6324):1263, Apr. 24, 1982.
Article entitled "A New Temporary Pacing Electrode", by Robicsek et al, Copyright 1980 by the Society of Thoracic Surgeons.

*Primary Examiner*—Lee S. Cohen
*Attorney, Agent, or Firm*—Benasutti and Murray

[57] ABSTRACT

An apparatus and method for effecting cardiac pacing capture utilizes an in-place catheter having at least one lumen terminating in a distal port which is positioned within a pre-selected heart chamber. The other end of the lumen terminates in a proximal port which is connected to a cannular connector containing an adjustable seal having a distal portion of a wire electrode extending therethrough. The seal is loosened and the wire electrode is advanced through it and the catheter lumen until its distal end emerges from the distal port of the in-place catheter and engages a surface of the heart chamber. The seal is re-tightened if desired; for example, to continuously monitor pressure by means of a pressure monitor connected to a port in the cannular connector. The proximal end of the wire electrode is connected to the output of a pacemaker pulse generator. The output of the pacemaker pulse generator is set to a level at which cardiac pacing capture is achieved.

16 Claims, 5 Drawing Figures

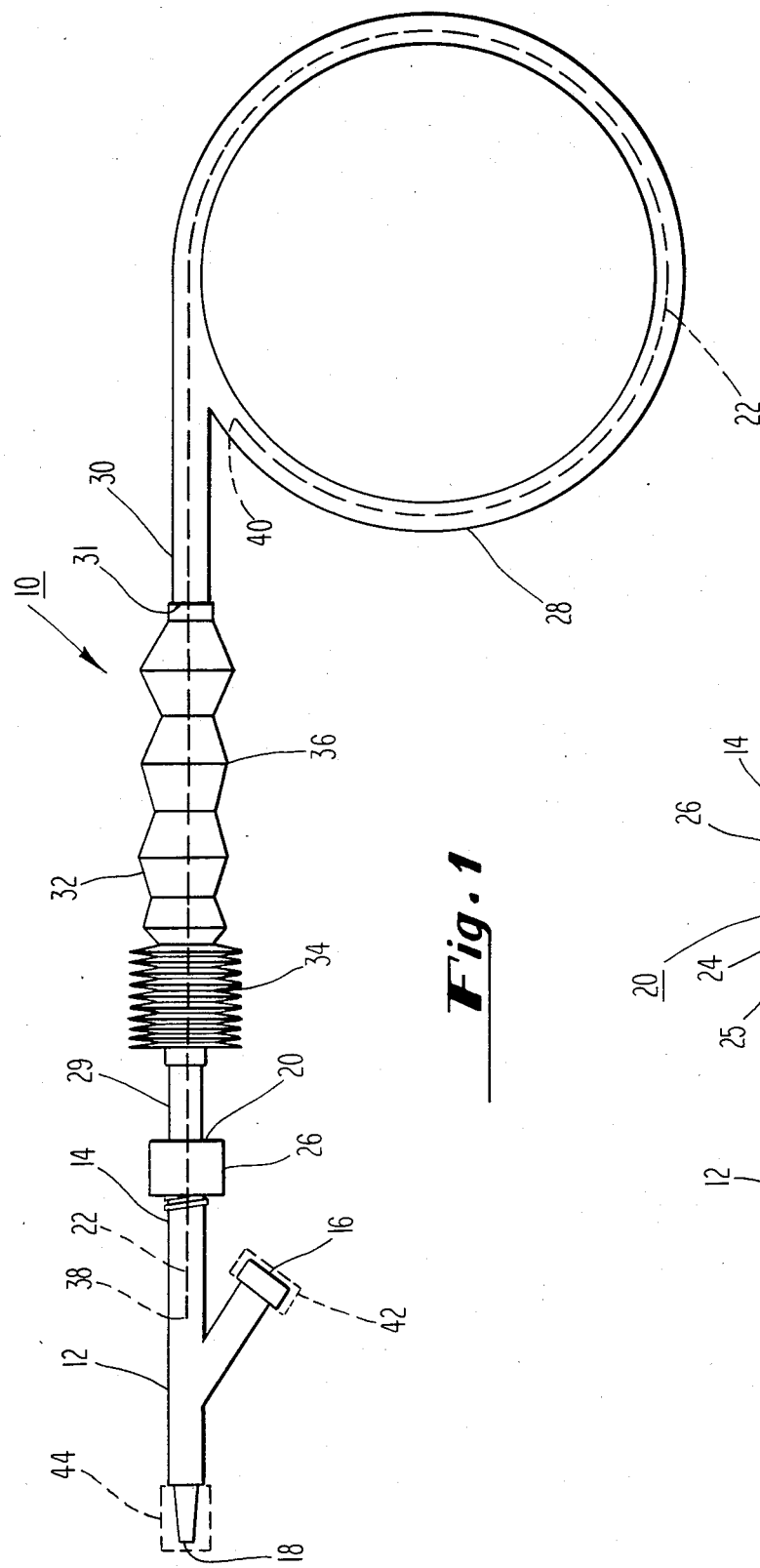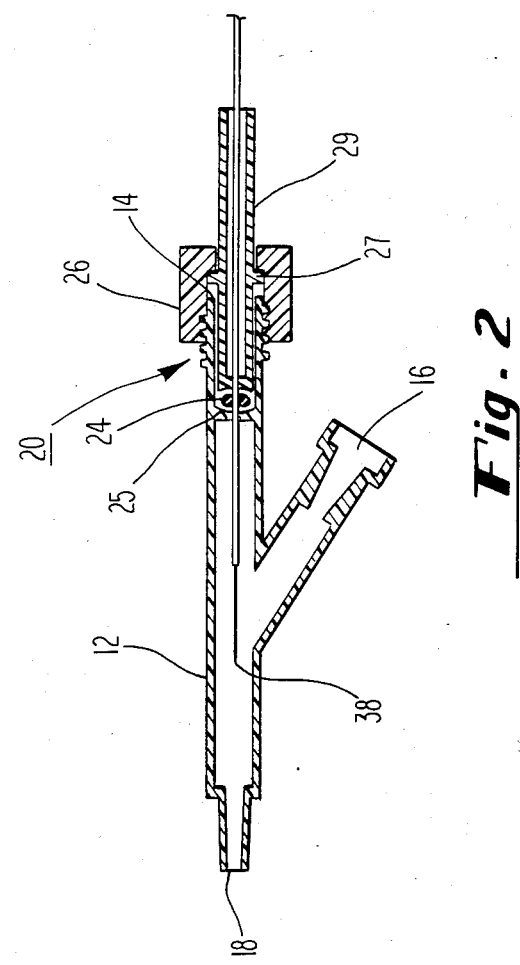

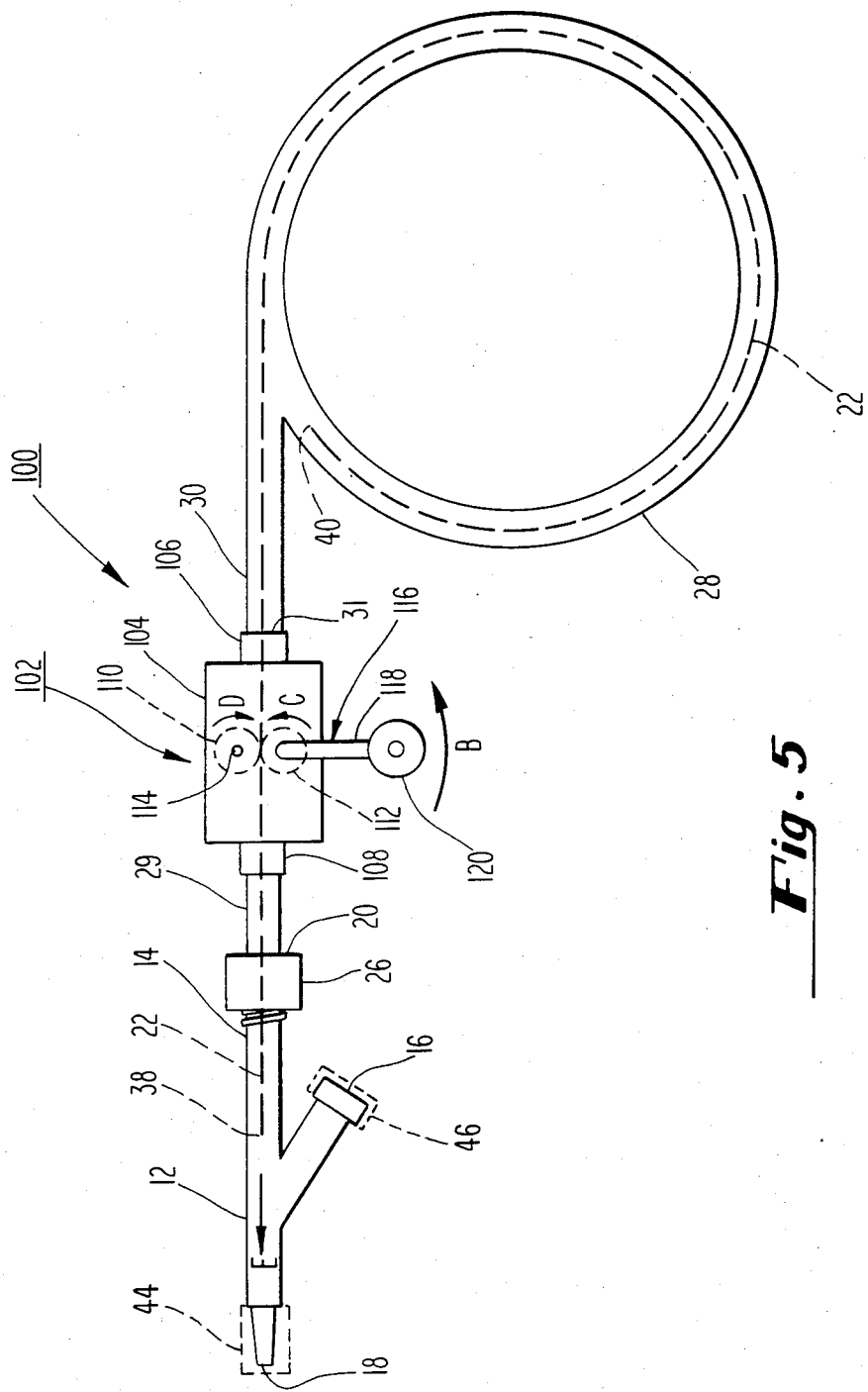

METHOD AND APPARATUS FOR CONVERTING A CATHETER TO A CARDIAC PACING ELECTRODE

This invention relates to cardiac pacing apparatus and methods of utilization thereof; and more specifically to cardiac pacemaker electrode insertion methods and apparatus.

Bradyarrythmias requiring pacing can occur unexpectedly during pulmonary artery catheter insertion; as well as in operative or post operative cardiac patients, in patients who have suffered myocardial infarction, or in other critically ill patients with pulmonary artery catheters in place. Bradyarrythmias may also develop in cardiac catherization patients, especially during contrast cineangiography.

Unless pacing electrodes (for example epicardial, transvenous or pacing type catheters) are already in place, emergency transvenous or transthoracic pacing may be required. Both of these techniques require a relatively long period of time and a considerable amount of expertise. Although the requisite expertise may be available, time, in these situations, is always a critical factor. Under emergency conditions, even an experienced practitioner can encounter difficulties when utilizing these prior art techniques to insert a pacing electrode into the proper location and effect electrode placement sufficient to enable cardiac pacing. The more difficulties encountered, the longer it takes to achieve pacing and the less the patient's chances of survival become. Consequently, it is desireable that the technique for inserting pacing electrodes be effected easily, with minimal effort, and in the least possible time.

It is an object of the present invention to provide a method and apparatus for providing cardiac pacing of patients having a cardiac catheter in place.

It is another object of the present invention to provide a method and apparatus for inserting cardiac pacing electrodes which is simple, rapid and reliable.

It is still another object of the present invention is to provide a method and apparatus for inserting cardiac pacing electrodes which requires relatively little operator skill.

SUMMARY OF THE INVENTION

The present invention provides a method and apparatus for providing cardiac pacing to those patients having cardiac catheters in place, the in-place catheter having at least one lumen disposed therein. The apparatus includes a pacing electrode comprising an electrically conductive, insulated wire having the insulation removed from a portion of each end. The wire electrode is stored in coiled form within a sterile storage container, with the distal end of the wire electrode extending through an O-ring seal of a cannular Y connector. The Y connector is interposeable between the in-place catheter and its associated monitoring device.

To use, the operator removes the monitoring device from the in-place catheter and interposes the Y connector therebetween. In one method, assuming that the distal part of the catheter was in place within the pulmonary artery and the monitoring device measures fluid pressure, the catheter is withdrawn into the right ventricle using pressure criteria. The wire electrode is then advanced through the O-ring seal of the Y connector and into the catheter lumen. The wire electrode is advanced through the catheter lumen until the distal end emerges from the distal port of the catheter, as indicated by distance marks on the wire electrode. Advancement of the wire electrode is continued until the distal end emerges the ventricular endocardium. The proximal end of the wire electrode is electrically connected to one output terminal of a demand pacemaker pulse generator. The other output terminal of the demand pacemaker pulse generator is connected to a skin electrode. The output of the pulse generator is increased until cardiac pacing capture is achieved.

In another method, again assuming that the distal port of the catheter was in position within the pulmonary artery, the wire electrode is advanced through the O-ring seal and the catheter lumen until the distal end emerges from the distal port of the catheter. The proximal end of the wire electrode is electrically connected to the pulse generator output which is referenced to the skin as previously described. With the pulse generator set at high output, the catheter, with the wire electrode protruding therefrom, is withdrawn from the pulmonary artery into the right ventricle using known distance criteria. If pacing capture does not occur, the catheter and electrode are manipulated within the right ventricle until capture occurs.

In yet another method, once again assuming that the distal port of the catheter was in position within the pulmonary artery, the catheter is withdrawn from the pulmonary artery, through the right ventricle into the right atrium using pressure criteria. The wire electrode is then advanced through the O-ring seal and the catheter lumen until the distal end exits the catheter and contacts the right atrial endocardium. The proximal end of the wire electrode is then electrically connected to the pacemaker pulse generator output which is referenced to the skin as previously described. The output of the pulse generator is increased until atrial pacing is achieved.

In still another method, this time assuming that the distal end of the catheter is in place within the left ventricle, the wire electrode is advanced through the O-ring seal and catheter lumen until the distal end exits the catheter and contacts the left ventricular endocardium. The proximal end of the wire electrode is electrically connected to the pulse generator output which is referenced to the skin as previously described. The output of the pulse generator is increased until cardiac pacing capture is achieved.

BRIEF DESCRIPTION OF THE DRAWING

FIG. 1 is a side view showing one embodiment of a cardiac pacing electrode insertion apparatus in acordance with the present invention.

FIG. 2 is a sectional view of a Y connector portion of the cardiac pacing electrode apparatus depicted in FIG. 1.

FIG. 5 is a side view showing another alternate embodiment of the cardiac pacing electrode insertion apparatus in accordance with the present invention.

DESCRIPTION OF THE PREFERRED EMBODIMENT

Figure 3:
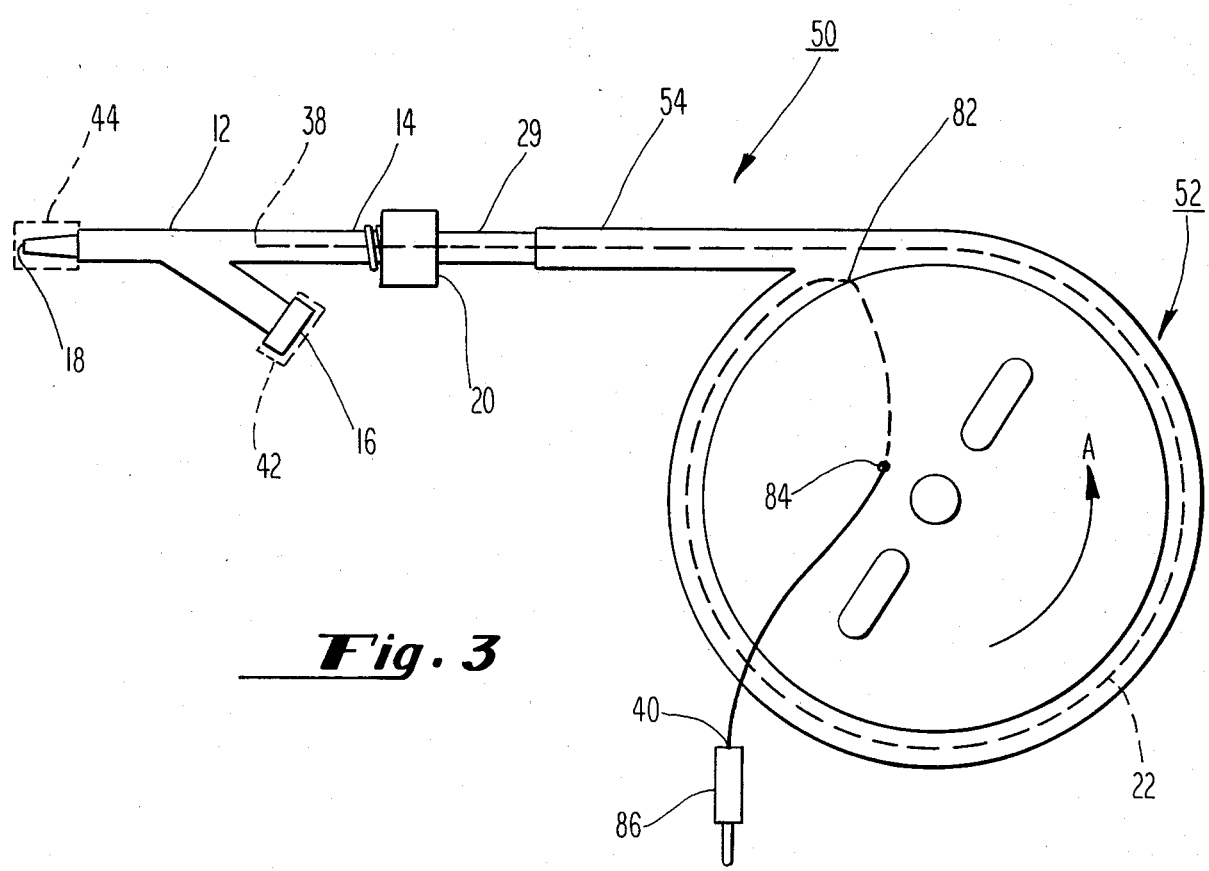
FIG. 3 is a side view showing an alternate embodiment of the cardiac pacing electrode insertion apparatus in accordance with the present invention.

Referring to FIG. 1 there is shown a cardiac pacing electrode insertion apparatus 10 which comprises a cannular Y connector 12 having a first port 14, a second port 16 and a third port 18. The Y connector 12 is preferably constructed of a rigid, heat and impact resistant transparent plastic material such as polystyrene. The first port 14 is equipped with an adjustable seal 20, preferably a compressible O-ring type. The adjustable seal 20 functions to provide a seal around an insulated wire electrode 22 which is inserted therethrough. The wire electrode 22 is preferably a fixed core, flexible tip spring guide wire, 125 cm in length and 0.457 mm in diameter, and coated with a synthetic resin polymer such as TEFLON.

As shown more clearly in FIG. 2, the adjustable seal 20 preferably comprises an O-ring 24 which is compressible against a seat 25 by means of a threaded knob 26. The wire electrode 22 passes through the O-ring and when the knob 26 is tightened, it acts against a shoulder portion 27 of a hollow sleeve 29, forcing the sleeve 29 to compress the O-ring 24 against the seat 25, which in turn causes the formation of an air-tight seal about the wire electrode 22. When the knob 26 is loosened, the O-ring 24 expands permitting the wire electrode 22 to slide therethrough. It is preferred that the O-ring 24 be constructed of a compressible, heat resistant, resilient material, for example neoprene; and that the remaining components of the adjustable seal 20 be constructed of a rigid, heat and impact resistant, transparent plastic material such as polystyrene.

In the embodiment shown in FIG. 1, the wire electrode 22 is coiled within a wire storage tube 28, which is preferably made of a heat resistant, plastic material such as polyvinyl chloride. The wire electrode 22 has a distal end 38 and a proximal end 40. In the preferred embodiment, the insulation is removed from each of these ends for a distance of approximately five millimeters. In addition, it is preferred that the wire electrode 22 be provided with appropriate markings indicating distance from the distal end 38.

The wire storage tube 28 has an outlet 30 having an outlet port 31 which is circumferentially sealed by one end of a wire electrode advancing means comprising a cylindrical accordion sleeve 32. The other end of the accordion sleeve 32 is sealed about the sleeve 29, thereby providing a sterile enclosure for that portion of the wire electrode 22 which extends out of the wire storage tube 28 into the Y connector 12. The accordion sleeve 32, is preferably constructed using a thin, transparent and easily deformable material such as cellophane. As shown in FIG. 1, the accordion sleeve 32 has a gathered portion 34 adjacent the adjustable seal 20 and an extended portion 36 which extends from the gathered portion 34 to the outlet 30 of the tube 28. The second and third openings, 16 and 18, of the Y connector 12 are preferably sealed with removeable caps 42 and 44 respectively in order to establish a sterile field within the entire apparatus 10 prior to use.

The electrode insertion device 10 is used in conjunction with an in-place cardiac catheter as follows. The sealing caps 42 and 44 are removed from the second 16 and third 18 ports of the Y connector 12. The monitoring device, usually a pressure transducer, is removed from the proximal end of the in-place catheter (not shown). The third port 18 of the Y connector 12 is thereupon connected to the proximal end of the in-place catheter, with the pressure transducer being connected to the second port 16 of the Y connector 12. Assuming the knob 26 of the adjustable seal 20 had been previously tightened, the catheter is still useable for its nominal pressure sensing function since there is a seal formed between the wire electrode 22 and the first port 14 as previously described.

Upon completion of the aforementioned connections, one of at least the following four described methods can be used to achieve cardiac pacing capture, depending upon the location of the catheter within the heart and whether the electrode insertion is under elective or emergency conditions.

Method 1—Elective insertion into the right ventricle of the heart through the lumen of a previously inserted pulmonary artery (PA) catheter. The PA catheter is withdrawn, while continuously monitoring the pressure, until a pulmonary artery to right ventricular pressure transistion is observed. The distal tip of the catheter is now located in the right ventricle. The knob 26 of the adjustable seal 20 is loosened until the wire electrode 22 can be slipped therethrough. The operator then grasps the accordion sleeve 32 just behind the gathered portion 34 and withdraws the accordion sleeve 32, causing the extended portion 36 to gather and the gathered portion 34 to extend. The operator then grasps the wire elecrode 22 through the sleeve 32 and advances the wire electrode 22 through the adjustable seal 20 as far as permitted by the stroke of the accordion sleeve 32. The operator then releases the wire electrode 22, withdraws the accordion sleeve 32 again and repeats the process until the distal end 38 of the wire electrode 22 exits the distal end of the in-place catheter. This can be determined by a distance marks predisposed on the wire electrode 22 as previously described. Advancement of the wire electrode continues until the distal end 38 engages the ventricular endocardium.

After the distal end 38 of the wire electrode 22 has exited the distal end of the catheter and engaged the ventricular endocardium, the remainder of the wire electrode 22 is withdrawn from the storage tube 28 by separating the tube 29 from the sleeve 32 and, while holding the wire electrode 22 in place, pulling on the tube 28 until the proximal end 40 of the wire electrode 22 is clear. The exposed proximal end 40 of the wire electrode 22 is then electrically connected to the cathode of a demand pacemaker pulse generator (not shown). The anode of the pulse generator is electrically connected to a skin electrode (not shown), preferably a pre-gelled electrocardiogram skin electrode. The pulse generator is then turned on and its output is increased until cardiac pacing capture is achieved as detected by a heart beat monitor, for example an electrocardiogram display.

Method 2—Emergency insertion into the right ventricle through a previously inserted PA catheter. This method is indicated in those patients exhibiting episodes of asystole or extreme bradycardia where pressure guidance may not be possible. The wire electrode 22 is advanced through the lumen of the PA cathether until the distal end 38 emerges from the opening in the distal tip of the catheter as indicated by the distance marks on the wire electrode. The advancement of the wire electrode 22 through the lumen of the catheter is accomplished as previously described with respect to Method 1. The proximal end of the wire electrode 22 is then electrically connected to the output of a pulse generator referenced to the skin as also described in Method 1. With the pulse generator on and set at high output (for example 10 milliamps), the PA catheter is then withdrawn from the pulmonary artery into the right ventricle using known distance criteria. If pacing capture does not occur once the electrode is known to be positioned within the right ventricle, the catheter and the electrode are manipulated until capture does occur.

Method 3—Emergency insertion into the left ventricle in patients requiring pacing during left heart catheterization. This method is indicated in those patients undergoing diagnostic catherization to assess the presence or severity of coronary artery disease. This method is specially indicated in those patients developing bradyarrythmias during contrast cineangiography. The left heart cathether is positioned with its tip within the left ventricle. The wire electrode 22 is advanced through the left heart catheter, using the procedure described for advancement with respect to Method 1, until its distal end 38 exits the catheter to contact the left ventricular endocardium. The pulse generator output is electrically connected to the proximal end of the wire electrode 22 and referenced to the skin as described in Method 1. The pulse generator is then turned on and its output is increased until pacing capture is achieved.

Method 4—Elective right atrial pacing in patients with a previously inserted PA catheter. The PA catheter is withdrawn from the pulmonary artery to the right atrium under pressure control, first observing the pulmonary artery to right ventricular pressure transition, then ceasing withdrawal after observing the transition of right ventricular to right atrial pressure. The catheter tip is now located in the right atrium. The wire electrode 22 is advanced through the lumen in the same manner as described with respect to Method 1, until the distal end 38 exits the catheter tip and contacts the right atrial endocardium. The pulse generator output is then electrically connected to the proximal end 40 of the wire electrode 22 and referenced to the skin as described in Method 1. The pulse generator is turned on and its output is increased until cardiac pacing capture is achieved.

Referring to FIG. 3 there is shown an alternate embodiment of the cardiac pacing electrode insertion apparatus of the present invention, generally referred to as 50. In this embodiment, the wire electrode 22 is coiled in a wire electrode advancing means comprising a reel-type container generally referred to as 52, having an outlet 54. It is preferred that the reel-type container 52 be constructed of a rigid, heat and impact resistant, transparent plastic material such as polystyrene. The outlet 54 is connected to the sleeve 29 which is disposed in the first port 14 of the Y connector 12.

The distal end 38 of the wire electrode 22 is threaded through outlet 54 and through the adjustable seal 20 into the cannular Y connector 12 in the same manner as previously described with respect to the first embodiment 10. Thus, the combination of reel-type container 52, outlet 54 and Y connector 12, having removeable caps 42 and 44 installed on the second and third ports 16 and 18, form a sterile package for at least that portion of the wire electrode 22 which is advanced into the catheter lumen.

Figure 4:
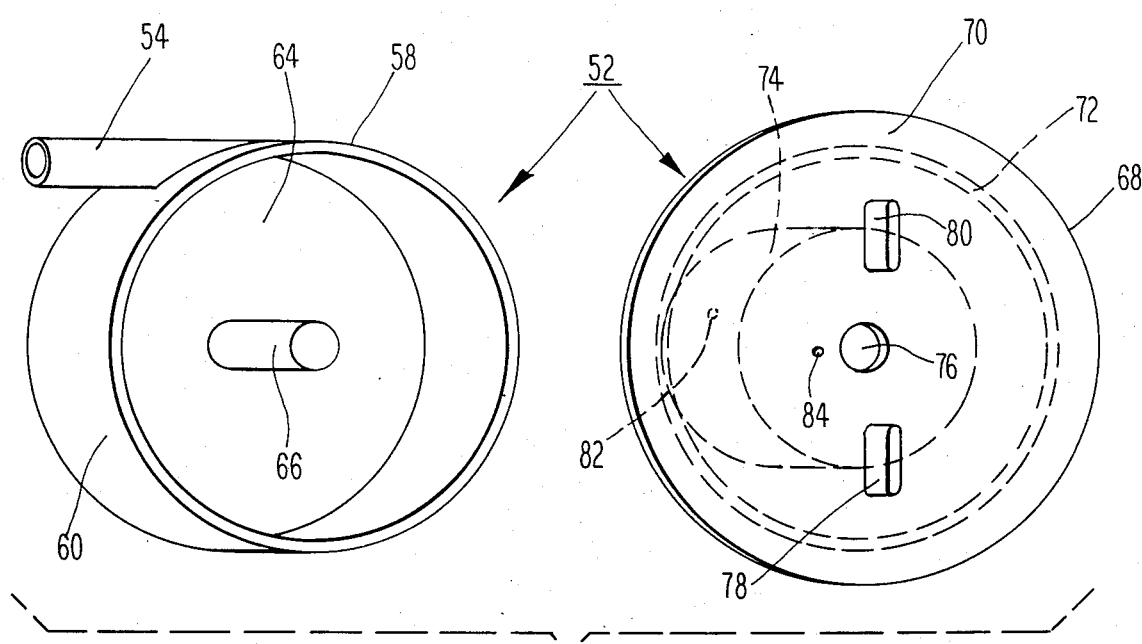
FIG. 4 is a perspective view of a reel-type container portion of the cardiac pacing electrode apparatus depicted in FIG. 3.

Referring now to FIG. 4, the preferred embodiment of the reel-type container 52 comprises a first half 58 which is a hollow drum portion with a peripheral wall 60 for enclosing a coiled length of the electrode wire 22. The drum portion 58 also includes a rear wall 64, a hub 66, and the outlet 54. The outlet 54 is preferably integrally molded as part of the first half 58. The outlet 54 defined a cylindrical passage which is connected to the sleeve 29 disposed in the first port 14 of the Y connector 12. To maintain sterility, the outlet 54 is preferably sealed to the sleeve 29.

The second half of the container 52 is designated 68 and comprises disc-shaped front wall 70 having an outer diameter is slightly larger than the outer diameter of the peripheral wall 60 of drum portion 58. The front wall 70 contains a circular recess 72 in the inner surface thereof. The circular recess is sized to receive the edge of the peripheral wall 60 when the first and second halves 58 and 68 are mated together. The second half 68 also includes a circular core 74 extending from the inner surface of the front wall 70. The length of the core 74 is sized such that its end superficially engages the inner surface of the rear wall 64 when the first and second halves 58 and 68 are mated together. The front wall 70 contains an aperture 76 adapted to frictionally engage the hub 66. In an alternative embodiment, the hub 66 is hollow and sized to fit through the aperture 76. The hollow portion of the hub 66 is dimensioned to frictionally receive a retainer pin having a shoulder which retains the first and second halves, 58 and 68, in a rotatable mating relationship.

A pair of finger grips 78 and 80 extend from the outer surface of the front wall 70 of the second half 68. These finger grips enable the second half 68 of the reel-type container 52 to be manually rotated within the first half 58 in order to effect the advancement of the wire electrode 22 out of the container 52 through the cannular Y connector 12 as will be subsequently described.

The wire electrode 22 is coiled around the core 74, thereby placing the coiled wire 22 in the space defined by the peripheral wall 60 of the first half 58 and the core 74 of the second half 68 of the reel-type container 52. The proximal end 40 of the wire electrode 22 extends through an aperture 82 in the core 74 then exits the reel-type container 52 through an aperture 84 in the front wall 70 of the second half 68. This permits access to the proximal end 40 of the wire electrode 22 for electrical connection to the demand pacemaker pulse generator. It is preferable that the proximal end 40 of the wire electrode 22 terminate in a connector 86 which is compatible with the pulse generator output terminal.

The tendency of the coiled wire electrode 22 to fly apart forces it against the peripheral wall 60 so that movement of the core 74 by manually rotating the second half 68, using for example the finger grips 78 and 80, results in the coiled wire moving also. Since the wire electrode 22 is threaded through the outlet 54 in the first half 58, it is seen that rotating the second half 68 in the direction indicated by arrow "A" with respect to the first half 58 will force the coiled wire electrode 22 out of the container 52, and through the Y connector 12 and the catheter lumen in a smooth manner.

This reel-type motion is utilized, in this alternate embodiment of the apparatus, to advance the wire electrode 22 through the in-place catheter to accomplish the methods previously described. Thus the wire electrode advancement means of this embodiment comprises the container 52 having a core portion rotatably disposed within a drum portion wherein the actuator is the core portion which serves to reel the coiled wire electrode out of the hollow space within the container 52 formed between the drum and core portions, through the Y connector 12 and the catheter lumen. The proximal end 40 of the wire electrode 22, which extends through the aperture 84 in the core portion, is electrically connected to the pulse generator output as previously described.

Referring to FIG. 5, there is shown another alternate embodiment of the cardiac pacing electrode insertion apparatus of the present invention, generally referred to as 100. In this embodiment, the wire electrode advancing means comprises an electrode advancing crank, generally referred to as 102, having a crank housing enclosure 104. The housing enclosure 104 is preferably constructed of a rigid, impact resistant, transparent plastic material such as polystyrene. An inlet port 106 is disposed through one end of the crank housing 104 and an outlet port 108 is disposed through the opposite end. The outlet port 31 of the outlet 30 of the wire storage tube 28 is connected to the inlet port 106 of the crank housing 104. The outlet port 108 is connected to the sleeve 29 of the adjustable seal 20.

The housing 104 contains an idler roller 110 and a drive roller 112 in engaging relationship one to the other. The idler roller 110 rotates about an axle 114 which is attached to the walls of the housing 104. The drive roller 112 is secured to a drive axle (not shown) which is rotatably mounted within the housing 104 in spaced relation to the axle 114 such that the surface of the drive roller 112 contacts the surface of the idler roller 110 in frictional engagement therewith. It is preferred that the dirve roller 112 and the idler roller 110 be constructed of a compressible, resilient material, for example neoprene, in order that the contacting surfaces compress and frictionally engage each other as well as the wire electrode 22 which is inserted therethrough. A crank 116, comprising a shaft 118 and a crank handle 120 which is rotatably attached to one end of the shaft 118, is rigidly attached to one end of the drive roller axle.

The electrode advancing crank 102 is used to advance the electrode 22 as follows. The wire electrode 22 extends out of the outlet port 31 of the storage tube 28, between the contacting surfaces of the drivere roller 112 and the idler roller 110, and into the Y connector 12 through the adjustable seal 20. After removing sealing cap 44 from the third port 18 of the Y connector 12, connecting the third port 18 to the proximal end of the in-place catheter, and releasing the adjustable seal 20, the wire electrode 22 is advanced into the in-place catheter by rotating the crank in the direction indicated by the arrow "B". This causes the drive roller 112 to rotate in the direction indicated by arrow "C", which causes the idler roller 110 to rotate in the direction indicated by the arrow "D". The rotating rollers withdraw the wire electrode 22 from the container 28 and advance it in the direction indicated by arrow "E". The crank is rotated until the distal end 38 of the wire electrode 22 emerges from the distal end of the in-place catheter as previously described.

From the above description it can be seen that the method of the present invention is rapid, reliable and requires relatively little operator skill. Sterile pre-packaging of the wire electrode within the apparatus facilitates its emergency insertion.

While the invention has been described primarily in terms of specific perferred embodiments thereof, it is not to be limited thereto but rather only to the extent set forth hereafter in the claims which follow.

I claim:

1. An apparatus for converting an in-place cardiac catheter to a pacing electrode, said catheter having at least one distal port at one end threof and at least one proximal port at the other end with a lumen connected therebetween, said distal port being positioned within a pre-selected heart chamber, said apparatus comprising:
   a. a wire electrode comprising a length of electrically conductive wire having a proximal end adapted for electrical connection to a pacemaker pulse generator and a distal end;
   b. a cannular connector having a first port containing adjustable sealing means adapted to receive and adjustable to a first position to permit said wire electrode therethrough and a second position to substantially prevent fluid transmission through said first port, and at least a second port adapted to matingly engage the proximal port of said catheter; and
   c. means for advancing said wire electrode through said adjustable sealing means, said cannular connector, said second port and said lumen, until the distal end of said wire electrode emerges from the distal port of said catheter and engages a surface of said heart chamber.

2. An apparatus in accordance with claim 1 wherein said cannular connector is substantially Y-shaped having a third port adapted to matingly engage a monitoring device.

3. An apparatus in accordance with claim 1 wherein said wire electrode is disposed within a storage container having an outlet port, with at least a portion of said wire electrode extending therefrom into the first port of said cannular connector through said adjustable sealing means, and wherein said wire electrode advancing means comprises a deformable sleeve surrounding said wire electrode between said first port and said outlet port, said deformable sleeve adapted for reciprocal movement along at least a length of said wire electrode.

4. An apparatus in accordance with claim 3 wherein said deformable sleeve comprises a sleeve having at least one accordion pleat formed therein.

5. An apparatus in accordance with claim 4 wherein said cannular connector is substantially Y-shaped having a third port adapted to matingly engage a monitoring device.

6. An apparatus in accordance with claim 1 wherein said wire electrode advancing means comprises a reel-type container having a first half with an outlet port connected to the first port of said cannular connector and a second half having a core about which at least a portion of said wire electrode is coiled, said second half being rotatably connected to said first half whereby rotation of said second half with respect to said first half causes said wire electrode to emerge from said outlet port.

7. An apparatus in accordance with claim 6 wherein the proximal end of said wire electrode extends external to said reel-type container through an aperture in said second half.

8. An apparatus in accordance with claim 1 wherein said wire electrode is disposed within a storage container having an outlet port, with at least a portion of said wire electrode extending therefrom into the first port of said cannular connector through said adjustable sealing means, and wherein said wire electrode advancing means comprises an electrode advancing crank including:

a. a crank housing disposed around said wire electrode between said first port and said outlet port; and b. a drive roller and an idler roller mounted within said crank housing, said rollers adapted to engage said wire electrode therebetween whereby rotation of said drive roller causes said wire electrode to be withdrawn from said storage container.

9. An apparatus in accordance with claim 8 wherein said electrode advancing crank additionally comprises a crank handle connected to said drive roller.

10. A method of cardiac pacing utilizing an in-place catheter having at least one distal port adjacent one end thereof and at least one proximal port at the other end with a lumen connected therebetween, said distal port being positioned within a pre-selected heart chamber, said method comprising the steps of:

a. providing a wire electrode comprising a length of electrically conductive wire having a proximal end adapted for electrical connection to a pacemaker pulse generator and a distal end;

b. providing a cannular connector having a first port containing adjustable sealing means adapted to receive and adjustable to a first position to permit said wire electrode therethrough and a second position to substantially prevent fluid transmission through said first port, and at least a second port adapted to matingly engage the proximal port of said catheter;

c. connecting the second port of said cannular connector to the proximal port of said catheter;

d. causing the distal end of said wire electrode to emerge from the distal port of said catheter and engage a surface of said heart chamber by advancing said wire electrode through said adjustable sealing means, said second port of said cannular connector and said catheter lumen; and e. attaching the proximal end of said wire electrode to said pacemaker pulse generator and adjusting the generator output until pacing capture is achieved.

11. A method of cardiac pacing utilizing an in-place catheter having at least one distal port adjacent one end thereof and at least one proximal port at the other end with a lumen connected therebetween, said distal port being positioned within a pulmonary artery, said method comprising the steps of:

a. providing a wire electrode comprising a length of electrically conductive wire having a proximal end adapted for electrical connection to a pacemaker pulse generator and a distal end;

b. providing a cannular connector having a first port containing adjustable sealing means adapted to receive and adjustable to a first position to permit said wire electrode therethrough and a second position to substantially prevent fluid transmission through said first port, and at least a second port adapted to matingly engage the proximal port of said catheter;

c. connecting the second port of said cannular connector the proximal port of said catheter;

d. withdrawing the distal port of said catheter from said pulmonary artery into a pre-selected heart chamber;

e. causing the distal end of said wire electrode to emerge from the distal port of said catheter and engage a surface of said heart chamber by advancing said wire electrode through said adjustable sealing means, said second port of said cannular connector and said catheter lumen; and f. electrically connecting the proximal end of said wire electrode to said pacemaker pulse generator and adjusting the output thereof until pacing capture has been achieved.

12. A method of accordance with claim 11 wherein step d comprises withdrawing the distal port of said catheter from the pulmonary artery into said pre-selected heart chamber using distance criteria.

13. A method in accordance with claim 11 wherein step d additionally comprises the steps of:

a. providing a third port in said cannular connector adapted to matingly engage a fluid pressure monitoring device;

b. connecting a fluid pressure monitoring device to said third port; and c. withdrawing the distal port of said catheter from the pulmonary artery into said pre-selected heart chamber using pressure criteria as indicated on said fluid pressure monitoring device.

14. A method of cardiac pacing utilizing an in-place catheter having at least one distal port adjacent one end thereof and at least one proximal port at the other end with a lumen connected therebetween, said distal port being positioned within a coronary artery, said method comprising the steps of:

a. providing a wire electrode comprising a length of electrically conductive wire having a proximal end adapted for electrical connection to a pacemaker pulse generator and a distal end;

b. providing a cannular connector having a first port containing adjustable sealing means adapted to receive and adjustable to a first position to permit said wire electrode therethrough and a second position to substantially prevent fluid transmission through said first port, and at least a second port adapted to matingly engage the proximal port of said catheter;

c. connecting the second port of said cannular connector to the proximal port of said catheter;

d. causing the distal end of said wire electrode to emerge from the distal port of said catheter into said coronary artery by advancing said wire electrode through said adjustable sealing means, said second port of said cannular connector and said catheter lumen; and e. electrically connecting the proximal end of said wire electrode to said pacemaker pulse generator and adjusting the generator output until pacing capture is achieved.

15. A method of cardiac pacing utilizing an in-place catheter having at least one distal port adjacent one end thereof and at least one proximal port at the other end with a lumen connected therebetween, said distal port being positioned within a coronary artery, said method comprising the steps of:

a. providing a wire electrode comprising a length of electrically conductive wire having a proximal end adapted for electrical connection to a pacemaker pulse generator and a distal end;

b. providing a cannular connector having a first port containing adjustable sealing means adapted to receive and adjustable to a first position to permit said wire electrode therethrough and a second position to substantially prevent fluid transmission through said first port, and at least a second port adapted to matingly engage the proximal port of said catheter;

c. connecting the second port of said cannular conenctor to the proximal port of said catheter;

d. withdrawing the distal port of said catheter from said coronary artery into an aorta proximal to an aortic valve;

e. advancing the distal port of said catheter through said aortic valve into a pre-selected heart chamber;

f. causing the distal end of said wire electrode to emerge from the distal port of said catheter and engage a surface of said heart chamber by advancing said wire electrode through said adjustable sealing means, said second port of said cannular connector and said catheter lumen; and g. electrically connecting the proximal end of said wire electrode to said pacemaker pulse generator and adjusting the output thereof until pacing capture has been achieved.

16. A method of cardiac pacing utilizing an in-place catheter having at least one distal port adjacent one end thereof and at least one proximal port at the other end with a lumen connected therebetween, said distal port being positioned within an aorta, said method comprising the steps of:

a. providing a wire electrode comprising a length of electrically conductive wire having a proximal end adapted for electrical connection to a pacemaker pulse generator and a distal end;

b. providing a cannular connector having a first port containing adjustable sealing means adapted to receive and adjustable to a first position to permit said wire electrode therethrough and a second position to substantially prevent fluid transmission through said first port, and at least a second port adapted to matingly engage the proximal port of said catheter;

c. connecting the second port of said cannular connector to the proximal port of said catheter;

d. advancing the distal port of said catheter from said aorta through an aortic valve into a pre-selected heart chamber;

e. causing the distal end of said wire electrode to emerge from the distal port of said catheter and engage a surface of said heart chamber by advancing said wire electrode through said adjustable sealing means, said second port of said cannular connector and said catheter lumen; and f. electrically connecting the proximal end of said wire electrode to said pacemaker pulse generator and adjusting the output thereof until pacing capture has been achieved.

* * * * *